(12) United States Patent
Leibovici

(10) Patent No.: US 8,500,678 B1
(45) Date of Patent: Aug. 6, 2013

(54) METHOD AND APPARATUS FOR APPLYING AN ANESTHETIC

(76) Inventor: Jacob Leibovici, Lighthouse Point, FL (US)

( * ) Notice: Subject to any disclaimer, the term of this patent is extended or adjusted under 35 U.S.C. 154(b) by 283 days.

(21) Appl. No.: 12/557,753

(22) Filed: Sep. 11, 2009

Related U.S. Application Data

(63) Continuation-in-part of application No. 11/636,859, filed on Dec. 11, 2006, now abandoned.

(60) Provisional application No. 60/733,757, filed on Mar. 7, 2006.

(51) Int. Cl.
*A61M 5/30* (2006.01)

(52) U.S. Cl.
USPC ............................................... 604/69

(58) Field of Classification Search
USPC ................. 604/82–92, 96, 181–243
See application file for complete search history.

(56) References Cited

U.S. PATENT DOCUMENTS 4,109,653 A * 8/1978 Kozam et al. ............... 604/191
6,312,412 B1 * 11/2001 Saied et al. ................. 604/191

* cited by examiner

*Primary Examiner* — Nicholas Lucchesi
*Assistant Examiner* — Pritesh Patel
(74) *Attorney, Agent, or Firm* — Kenneth L Tolar

(57) ABSTRACT

A method and an apparatus for applying an anesthetic include an elongated tubular housing having an upper end, a substantially hollow interior, and a lower end having an injection needle extending therefrom. A first chamber is formed within the housing interior for holding an anesthetic cartridge therein. A second chamber receives a cannister containing an endothermic gas that rapidly absorbs heat when released to the atmosphere. The cartridge is penetrated by a plunger that forces the anesthetic through the injection needle. A depressible trigger propels the gas through an outlet nozzle that is oriented to project a stream of gas along a delivery axis that intersects a delivery axis of the needle; therefore, the gas and anesthetic can be successively delivered to an injection site with minimal repositioning of the housing. Accordingly, a dental practitioner can initially disperse the endothermic gas onto the injection site to minimize any pain and discomfort associated with an injection. Subsequently, the practitioner inserts the needle into the deadened site and injects the anesthetic.

3 Claims, 1 Drawing Sheet

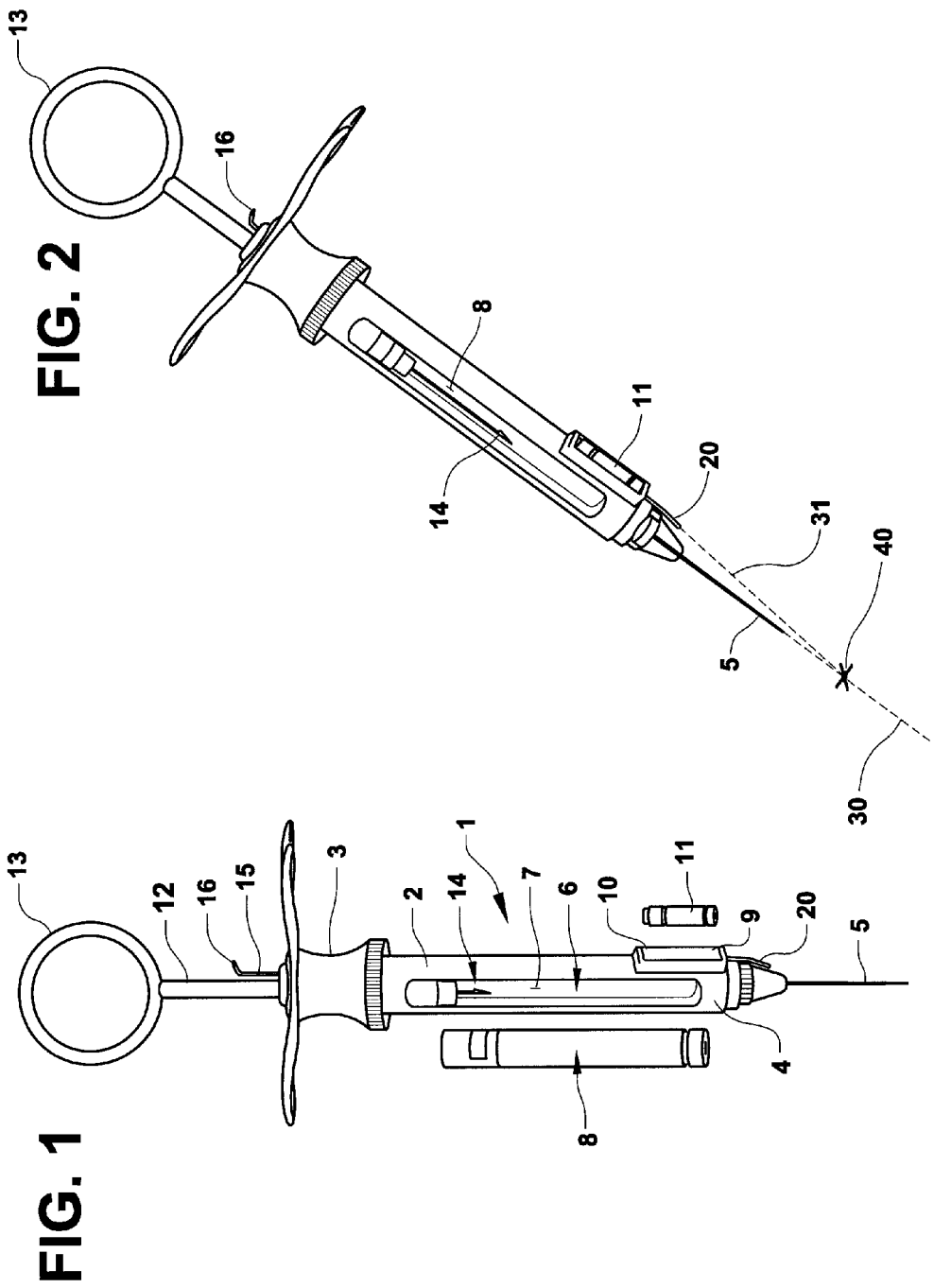

METHOD AND APPARATUS FOR APPLYING AN ANESTHETIC

CROSS REFERENCE TO RELATED APPLICATIONS

This application is entitled to the benefit of provisional application No. 60/733,757 filed on Mar. 7, 2006, and is a continuation-in-part of application Ser. No. 11/636,859, filed on Dec. 11, 2006, now abandoned, the specifications of which are incorporated herein by reference.

BACKGROUND OF THE INVENTION

The present invention relates to a method and apparatus for applying an anesthetic to a dental patient's gums.

DESCRIPTION OF THE PRIOR ART

A conventional dental syringe includes an anesthetic therein that is propelled through an injection needle with a depressible plunger. To minimize the pain that results when the injection needle penetrates a patient's gums, the dental practitioner will often apply a topical agent to the injection site using a cotton swab. Because the deadening agent is only applied topically, it is marginally effective. As a result, injecting an anesthetic often causes significant pain at the injection site. Accordingly, there is currently a need for a means of minimizing the pain associated with an anesthetic injection.

The present invention addresses this need by providing a dental syringe having an anesthetic cartridge and a compressed gas cannister therein. The cartridge includes a conventional dental anesthetic while the cannister includes a compressed, endothermic gas that rapidly absorbs heat when released to the atmosphere; the endothermic gas is first applied to the injection site prior to the anesthetic injection to minimize the pain associated with conventional anesthesia techniques. Furthermore, the gas also blanches the mucosa allowing a practitioner to readily identify the pretreated injection site so that the needle is not inserted into an unanesthetized area.

SUMMARY OF THE INVENTION

A method and an apparatus for applying an anesthetic include an elongated, tubular housing having an upper end, a substantially hollow interior, and a lower end having an injection needle extending therefrom. A pair of chambers are formed within the housing interior, each for holding either a cartridge or a small cannister therein. The cartridge contains a conventional dental anesthetic while the cannister includes a compressed, endothermic gas that temporarily deadens a proposed injection site upon contact. The cartridge is penetrated by a designated plunger that forces the anesthetic through the injection needle. The cannister includes a depressible trigger that propels the gas through an outlet nozzle that is oriented to project the gas along a delivery axis that intersects a delivery axis of the needle; as a result, the gas and the anesthetic can be successively delivered to an injection site with minimal repositioning of the housing. Accordingly, a dental practitioner can initially disperse the endothermic solution onto the injection site to minimize any pain and discomfort associated with an injection. Subsequently, the practitioner inserts the needle into the deadened site and injects the anesthetic.

It is therefore an object of the present invention to provide a dental syringe that minimizes the pain and discomfort caused by an anesthetic injection.

It is another object of the present invention to provide a dental syringe having an auxiliary cartridge for retaining and dispensing an antimicrobial endothermic solution.

It is yet another object of the present invention to provide a method of applying an anesthetic that overcomes the disadvantages associated with conventional anesthesia techniques.

Other objects, features, and advantages of the present invention will become readily apparent from the following detailed description of the preferred embodiment when considered with the attached drawings and the appended claims.

BRIEF DESCRIPTION OF THE DRAWINGS

FIG. 1 is a plan view of the dental syringe with the cartridge and cannister removed therefrom.

FIG. 2 is a plan view of the dental syringe with the cartridge and cannister installed in their corresponding chambers.

DESCRIPTION OF THE PREFERRED EMBODIMENT

The present invention relates to a method and apparatus of applying a dental anesthetic. The apparatus comprises an elongated tubular housing 1 having an outer wall 2, an upper end 3, a substantially hollow interior, and a lower end 4 having an injection needle 5 extending therefrom. On the housing outer wall is an elongated opening 6 in communication with an anesthetic chamber 7 formed within the housing interior. The anesthetic chamber receives a cartridge 8 having a conventional dental anesthetic stored therein.

The outer wall also includes a smaller opening 9 that is in communication with an adjunctive chamber 10 for receiving a cannister 11. The cannister includes an endothermic gas or "freeze spray" solution that rapidly absorbs heat when dispersed into the atmosphere.

Coaxially received within the anesthetic chamber is a plunger 12 having a thumb ring 13 at an upper end and a spear 14 at a lower end; the spear penetrates a membrane on the upper end of the anesthetic cartridge to force fluid therein into the injection needle.

Coaxially received within the adjunctive chamber is a depressible trigger 15 having a handle 16 at an upper end that protrudes from the upper end of the housing. Depressing the trigger propels the gaseous solution through an outlet nozzle 20 on the lower end of the housing. The nozzle 20 is oriented to project a stream of gas along a delivery axis 31 that intersects a delivery axis 30 of the needle, preferably at a point 40 immediately adjacent to the needle outlet. Accordingly, a practitioner can first deaden a proposed injection site and then immediately insert the needle with little movement or repositioning of the syringe.

The method of applying an anesthetic using the syringe described above includes initially dispersing the heat-absorbing, endothermic gas onto a proposed injection site by depressing the trigger. Because the heat-absorbing substance constricts blood flow at the injection site, temporary numbing occurs. Furthermore, additional benefits of the endothermic solution include mechanical contraction of the muscles which blocks the transmission of pain perception according to the Gate theory, antimicrobial and inhibition of the release of inflammatory substances such as prostaglandin and leukotrienes. The use of the endothermic "freeze spray" also temporarily distracts the patient by creating a "popping" noise that diverts the patient's attention away from any potential or anticipated pain. Finally, because the solution blanches the mucosa, a readily-visible target is created for insertion of the needle to assure that the deadened area is not bypassed.

When the practitioner observes that the injection site mucosa has been blanched, the site is effectively deadened and a painless, concomitant injection is possible. The practitioner then can quickly inject the dental anesthetic into the blanched injection site by inserting the injection needle and depressing the plunger. Because of the positioning of the gas nozzle and needle outlet, the dispersal of the gas and subsequent injection of anesthetic can be accomplished almost concurrently and with little or no pain to the patient.

The above described device is not limited to the exact details of construction and enumeration of parts provided herein. For example, though the adjunctive chamber is preferably integral with the anesthetic chamber, the auxiliary chamber could be a separate component. The endothermic gas should remove sufficient to heat to function as described without causing necrosis. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A dental syringe comprising:
   an elongated tubular housing having an outer wall, a substantially hollow interior, an upper end and a lower end;
   an injection needle extending from the lower end of the housing;
   an anesthetic chamber within the hollow interior;
   an anesthetic cartridge received within said anesthetic chamber, said anesthetic cartridge having a dental anesthetic therein;
   an adjunctive chamber within said housing interior;
   a cannister received within said adjunctive chamber, said cannister having a compressed, endothermic gas therein that rapidly absorbs heat when released to the atmosphere;
   means for dispensing said anesthetic through said needle;
   an outlet nozzle in fluid communication with said cannister;
   means for dispensing said gas through said outlet nozzle.

2. The dental syringe according to claim 1 wherein said means for dispensing said anesthetic through said needle comprises:
   said anesthetic cartridge being in fluid communication with said needle;
   a plunger received within said anesthetic cartridge that, when depressed, forces anesthetic from said anesthetic cartridge into said needle.

3. The dental syringe according to claim 2 wherein said nozzle is oriented to project said gas along a delivery axis that intersects a delivery axis of the needle allowing said gas and said anesthetic to be successively delivered to an injection site with minimal repositioning of the housing.

\* \* \* \* \*